(12) United States Patent
Church et al.

(10) Patent No.: US 9,834,775 B2
(45) Date of Patent: Dec. 5, 2017

(54) RECOMBINANT CELLS AND ORGANISMS HAVING PERSISTENT NONSTANDARD AMINO ACID DEPENDENCE AND METHODS OF MAKING THEM

(71) Applicant: President and Fellows of Harvard College, Cambridge, MA (US)

(72) Inventors: George M. Church, Brookline, MA (US); Daniel J. Mandell, Brookline, MA (US); Marc J. Lajoie, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/025,406

(22) PCT Filed: Sep. 26, 2014

(86) PCT No.: PCT/US2014/057573
§ 371 (c)(1),
(2) Date: Mar. 28, 2016

(87) PCT Pub. No.: WO2015/048364
PCT Pub. Date: Apr. 2, 2015

(65) Prior Publication Data
US 2016/0230176 A1    Aug. 11, 2016

Related U.S. Application Data

(60) Provisional application No. 61/883,413, filed on Sep. 27, 2013.

(51) Int. Cl.
| | | |
|---|---|---|
| C12N 15/52 | (2006.01) | |
| C12N 1/36 | (2006.01) | |
| C12N 15/65 | (2006.01) | |

(52) U.S. Cl.
CPC ............. *C12N 15/65* (2013.01); *C12N 1/36* (2013.01); *C12N 15/52* (2013.01); *C12N 2800/22* (2013.01); *C12N 2840/102* (2013.01)

(58) Field of Classification Search
None
See application file for complete search history.

(56) References Cited

U.S. PATENT DOCUMENTS

2011/0195483 A1*  8/2011  Tian ..................... C12N 1/36
                                                    435/252.8
2013/0245230 A1    9/2013  Dieters et al.

FOREIGN PATENT DOCUMENTS

WO    2004/094593 A2    11/2004

OTHER PUBLICATIONS

Chaudhury et I., Bioinformatics, 2010, vol. 26(5) pp. 689-691.*
Chen et al., Nucleic Acids Research, 2005, vol. 33, pp. 3193-3199.*
Chaudhury et al. "PyRosetta: a script-based interface for implementing molecular modeling algorithms using Rosetta." Bioinformatics, Jan. 7, 2010 (Jan. 7, 2010), vol. 26. Iss. 5, pp. 689-691.
Mehl et al. Generation of a Bacterium with a 21 Amino Acid Genetic Code,• Journal of the American Chemical Society, Jan. 4, 2003 (Jan. 4, 2003), vol. 125, pp. 935-939.

* cited by examiner

*Primary Examiner* — Jennifer Dunston
(74) *Attorney, Agent, or Firm* — Banner & Witcoff, Ltd.

(57) ABSTRACT

Recombinant cells and recombinant organisms persistently expressing nonstandard amino acids (NSAAs) are provided. Methods of making recombinant cells and recombinant organisms dependent on persistently expressing NSAAs for survival are also provided. These methods may be used to make safe recombinant cells and recombinant organisms and/or to provide a selective pressure to maintain one or more reassigned codon functions in recombinant cells and recombinant organisms.

7 Claims, 18 Drawing Sheets
(17 of 18 Drawing Sheet(s) Filed in Color)

| Top performers | Day 1 Escapees / $10^7$ cells | |
|---|---|---|
| | mutS- | mutS+ |
| tyrS-D10 | 0 | 0 |
| tyrS-D11 | 0 | 0 |
| tyrS-des7 | 0 | 0 |
| adk-A4 | 4 | (0.04) |
| pgk-1-1-1 | 810 | (8.1) |
| metG-A2 | 110 | (1.10) |
| alaS-1 | 320 | (3.2) |

Figure 14

| Unnatural amino acid (UAA) | Common name (if applicable) | Organism(s) in which UAA is encoded[a] | References[b,c] (and notes) |
|---|---|---|---|
| 1 | p-Acetylphenylalanine | E. coli, yeast, mammalian cells | 66, 123, 131, 133 |
| 2 | m-Acetylphenylalanine | E. coli | 67 |
| 3 | | E. coli | 68 |
| 4 | O-allyltyrosine | E. coli | 69 |
| 5 | Phenylselenocysteine | E. coli | 70 (precursor to dehydroalanine) |
| 6 | p-Propargyloxyphenylalanine | E. coli, yeast, mammalian cells | 71, 125, 131, 133 |
| 7 | p-Azidophenylalanine | E. coli, yeast, mammalian cells | 72, 123, 128, 131, 133 |
| 8 | p-Bromophenylalanine | E. coli | 73 |
| 9 | | E. coli | H. Zeng & P.G. Schultz, unpublished |
| 10 | | E. coli | H. Zeng & P.G. Schultz, unpublished |
| 11 | | E. coli | M. Jahns & P.G. Schultz, unpublished |
| 12 | O-methyltyrosine | E. coli, yeast, mammalian cells | 74, 123, 124, 131, 133, 134 |
| 13 | p-Aminophenylalanine | E. coli | 64, 75 |
| 14 | p-Cyanophenylalanine | E. coli | 76 |
| 15 | m-Cyanophenylalanine | E. coli | J. Chittuluru & P.G. Schultz, unpublished |
| 16 | p-Fluorophenylalanine | E. coli | (80) (requires auxotrophic strain) |
| 17 | p-Iodophenylalanine | E. coli, yeast, mammalian cells | 78, 123, 131, 133 |
| 18 | p-Bromophenylalanine | E. coli | 77, 78, 139 |
| 19 | | E. coli | 79 |
| 20 | p-Nitrophenylalanine | E. coli | 80 |
| 21 | L-DOPA | E. coli | 81 |
| 22 | 3-Aminotyrosine | E. coli | 82 |
| 23 | 3-Iodotyrosine | E. coli, yeast, mammalian cells | 83, 132 |
| 24 | p-Isopropylphenylalanine | E. coli | 64 |
| 25 | 3-(2-Naphthyl)alanine | E. coli | 84 |
| 26 | Biphenylalanine | E. coli | 85 |
| 27 | | Yeast, mammalian cells | 126 |
| 28 | | Yeast, mammalian cells | 127 |
| 29 | | Yeast, mammalian cells | 130 |
| 30 | Homoglutamine | E. coli | 134 |
| 31 | D-tyrosine | E. coli | J. Gao & P.G. Schultz, unpublished |
| 32 | p-Hydroxyphenyllactic acid | E. coli | 86 (requires a strain with disrupted tyrR and aspC) |
| 33 | 2-Aminocaprylic acid | Yeast, mammalian cells | 89, 127 |
| 34 | Bipyridylalanine | E. coli | 85 |
| 35 | HQ-alanine | E. coli | 87 |
| 36 | p-Benzoylphenylalanine | E. coli, yeast, mammalian cells | 88, 123, 131, 133, 134, 169 |
| 37 | o-Nitrobenzylserine | Yeast, mammalian cells | 124 |

Figure 16

| Unnatural amino acid (UAA) | Common name (if applicable) | Organism(s) in which UAA is encoded[a] | References[b] (and notes) |
|---|---|---|---|
| 38 | o-Nitrobenzylserine | Yeast, mammalian cells | N. Wu & P.G. Schultz, unpublished |
| 39 | 4,5-Dimethoxy-2-nitrobenzylserine | Yeast, mammalian cells | 128 |
| 40 | o-Nitrobenzyllysine | E. coli, yeast, mammalian cells | 129 |
| 41 | o-Nitrobenzyltyrosine | E. coli | 89 |
| 42 | 2-Nitrophenylalanine | E. coli | 90 |
| 43 |  | E. coli | 91 |
| 44 |  | E. coli | 92 |
| 45 | Dansylalanine | Yeast, mammalian cells | 129, 134 |
| 46 |  | E. coli | 93 |
| 47 |  | Yeast, mammalian cells | 126; J. Guo, H.S. Lee, E.A. Lemke, R.D. Dimla, & P.G. Schultz, unpublished results |
| 48 | p-Carboxymethylphenylalanine | E. coli | 94 |
| 49 | 3-Nitrotyrosine | E. coli | 95 |
| 50 | Sulfotyrosine | E. coli | 96 |
| 51 | Acetyllysine | E. coli, yeast, mammalian cells | 114, 121 |
| 52 | Methylhistidine | Yeast, mammalian cells | F. Peters, J. Chaturvedi, & P.G. Schultz, unpublished |
| 53 | 2-Aminononanoic acid | Yeast, mammalian cells | 127 |
| 54 | 2-Aminodecanoic acid | Yeast, mammalian cells | 127 |
| 55 |  | Yeast, mammalian cells | 127 |
| 56 |  | Yeast, mammalian cells | 127 |
| 57 |  | Yeast, mammalian cells | 127 |
| 58 |  | Yeast, mammalian cells | 127 |
| 59 | Pyrrolysine | E. coli, yeast, mammalian cells | 111 (aaRS from a natural expanded genetic code) |
| 60 | Cbz-lysine | E. coli, yeast, mammalian cells | 112, 114 |
| 61 |  | E. coli, yeast, mammalian cells | 115 |
| 62 |  | E. coli, yeast, mammalian cells | 116, 129 |
| 63 |  | E. coli, yeast, mammalian cells | 115, 117 |
| 64 |  | E. coli, yeast, mammalian cells | 117 |
| 65 | Boc-lysine | E. coli, yeast, mammalian cells | 112, 114 |
| 66 |  | E. coli, yeast, mammalian cells | 118 |
| 67 | Allyloxycarbonyllysine | E. coli, yeast, mammalian cells | 112 |
| 68 |  | E. coli, yeast, mammalian cells | 112 |
| 69 |  | E. coli, yeast, mammalian cells | 116 |
| 70 |  | E. coli, yeast, mammalian cells | 119 |
| 71 |  | E. coli, yeast, mammalian cells | 119 |

[a] Underlined font, functionality not experimentally demonstrated but based on parent aminoacyl-tRNA synthetase (aaRS)/tRNA pair orthogonality.
[b] References are those pertinent to the original encoding of the UAA.
[c] Abbreviation: UAARS, UAA-specific cognate aminoacyl-tRNA synthetase.

Figure 16 (Cont.)

RECOMBINANT CELLS AND ORGANISMS HAVING PERSISTENT NONSTANDARD AMINO ACID DEPENDENCE AND METHODS OF MAKING THEM

RELATED APPLICATION

This application is a National Stage Application under 35 U.S.C. 371 of PCT application number PCT/US14/57573 designating the United States and filed Sep. 26, 2014; which claims the benefit of U.S. Provisional Patent Application No. 61/883,413, filed on Sep. 27, 2013, each of which are hereby incorporated by reference in their entireties.

STATEMENT OF GOVERNMENT INTERESTS

This invention was made with government support under EEC-0540879 awarded by National Science Foundation and under DE-FG02-02ER63445 awarded by U.S. Department of Energy and under N66001-12-C-4040 awarded by U.S. Department of Defense Space and Naval Warfare Systems Command. The Government has certain rights in the invention.

FIELD

The present invention relates in general to genetically modified cells and/or organisms.

BACKGROUND

Genetically modified organisms are increasingly used to produce human consumables such as fuels (e.g., ginkgo, LS9, SOLAZYME, Chromatin), commodity chemicals (e.g., GENENCOR, GENOMATICA, VERDEZYNE), and therapeutics (e.g., AMBRX, AMYRIS). They are also used in agriculture (e.g., GOLDEN RICE, ROUNDUP READY crops, FROSTBAN), bioremediation (e.g., oil spills), and healthcare (e.g., Crone's disease and oral inflammation). Although bio-containment strategies, such as engineered auxotrophy, induced lethality and gene flow prevention have been developed, selective pressure from leaky containment mechanisms can lead to bio-containment escape.

Genetically modified organisms provide unique opportunities to broaden the functional repertoire accessible to biotechnology. By reassigning the genetic code, organisms can produce proteins incorporating nonstandard amino acids (NSAAs) with properties not found in nature, resist viral infection due to mistranslated viral transcripts, and maintain genetic isolation from naturally coded organisms in their surroundings (F. J. Isaacs et al. (2011) Precise Manipulation of Chromosomes in Vivo Enables Genome-Wide Codon Replacement. *Science* 333:348). However, such organisms require unprecedented safety mechanisms to ensure their containment. Current best practices confer dependence on supplemented metabolites like diaminopimelic acid (DAP) (R. Curtiss (1978) Biological containment and cloning vector transmissibility. *Journal of Infectious Diseases* 137:668); J. Santander, W. Xin, Z. Yang, R. Curtiss (2010) The Aspartate-Semialdehyde Dehydrogenase of *Edwardsiella ictaluri* and Its Use as Balanced-Lethal System in Fish Vaccinology. *PLoS One* 5:e15944), an essential component of the cell wall, for survival. Since metabolites like DAP are natural products found in the environment, this strategy is insufficient to ensure containment of genetically modified organisms. Mutations that suppress NSAA dependence, acting either on the recoded genes or, more likely, on extent tRNAs (G. Eggertsson, D. Söll (1988) Transfer ribonucleic acid-mediated suppression of termination codons in *Escherichia coli. Microbiological Reviews* 52:354), will compromise any safety features that rely on genomic recoding.

Auxotrophies for natural metabolites like DAP or Thy are known in the art (R. Curtiss, Supra; J. Santander, Supra), but they lack sufficient safeguards. This is due to the fact that the metabolites can be found in nature, safety tests often focused only on the mammalian gut, and conjugation tests often considered only conjugation out from a genetically modified organism rather than into it, and did not address transduction by viruses and or phages.

Kill switches controlling genetically modified organism survival are known in the art (M. C. Ronchel, J. L. Ramos (2001) Dual system to reinforce biological containment of recombinant bacteria designed for rhizoremediation. *Applied and Environmental Microbiology* 67:2649), but these too lack sufficient safeguards. These genetically modified organisms have the potential for escape via failure of the killing mechanism and/or via broken circuitry (e.g., inactivation of repressors, activators, or other expression regulation mechanisms involved in the kill switch, loss of expression of a killing mechanism, constitutive activity of a survival mechanism and the like).

Methods of placing NSAAs at surface positions or near the 5' translation start site are also known, although these methods are also lacking. These methods incorporate natural amino acids at surface or terminal positions and are far less likely to disrupt folding and function, leaving clear routes to natural suppression (i.e., a natural tRNA mutates so that is can incorporate a natural amino acid at the desired position of the NSAA). Although escape can potentially be mitigated by placing NSAAs at very many surface and terminal positions, this complicates the approach relative to a much fewer number of high-impact core mutations and doesn't protect against suppressor mutations in which a natural amino acid is translated at the reassigned codon.

Horizontal and vertical gene transfer methods are also known. Agriculture and bioremediation use genetically modified organisms in the environment. However, methods are needed to prevent escape of herbicide/antibiotic resistant strains and to prevent cross-pollination and/or DNA transfer between genetically modified organisms and organic crops or other natural organisms.

Partial methods for reassigning the genetic code in order to efficiently incorporate NSAAs during translation are known (T. Mukai et al. (2010) Codon reassignment in the *Escherichia coli* genetic code. *Nucleic Acids Res.* 38:8188; D. Johnson et al., Rfl knockout allows ribosomal incorporation of unnatural amino acids at multiple sites. *Nat Chem Biol.* 7:779), but these methods are lacking. For example, partial recoding methods are not scalable/generalizable to other codons, because all genes would have to be duplicated using the target codon. Additionally, UAG function cannot be abolished because these methods do not remove all instances of UAG throughout the genome. Accordingly, such methods only swap codon function. Furthermore, these methods result in a strong selection pressure for natural suppressors, which leads to an unstable genetic code.

The engineering of organisms that can only grow safely in well-defined, restrictive environments has been a longstanding goal that dates back to the Asilomar Conference from 1975 and has yet to be achieved. Accordingly, recombinant cells, recombinant organisms (and methods of making them) that avoid unintended survival are needed.

SUMMARY

To prevent unintended survival of genetically modified cells and/or organisms, additional safeguards need to be implemented. For example, genetically modified organisms should contain modifications that cannot be escaped by complementation and cannot revert through natural mutation mechanisms. Genetic modifications should be sufficiently inexpensive to allow use in a large bioreactor for production of commodity chemicals. Genetic modifications should not adversely impact the stability, metabolic load, growth rate, or gene expression of the organism. Genetic modifications should extrapolate to industrially-relevant organisms.

Synthetic auxotrophy, whereby persistence of NSAA dependence is maintained in genetically modified organisms, is a promising approach for achieving these additional safeguards (FIG. 2). In order to ensure persistence of NSAA dependence, two complementary strategies are presented herein. A positive selection approach is provided herein whereby essential nucleic acid sequences (e.g., genes) encode an essential polypeptide sequence relying on the presence of one or more NSAAs in the polypeptide sequence to ensure translation, folding and/or proper function of the polypeptide (FIG. 1). A negative selection approach is provided herein whereby one or more toxins, toxic products, or polypeptides that produce or confer susceptibility to toxins or toxic products are misfolded and/or functionally impaired when an NSAA is present at a particular position of the one or more toxins, toxic products, or polypeptides that produce or confer susceptibility to toxins or toxic products. Each of these approaches may optionally be combined. These approaches, alone or in combination, provide an unprecedented safety mechanism that will advance humankind's ability to prevent unintended survival of genetically modified organisms.

Accordingly, in certain exemplary embodiments, a recombinant cell including an essential nucleic acid sequence (e.g., one, two or more essential nucleic acid sequences) encoding an essential polypeptide (e.g., one, two or more essential polypeptides) having a nonstandard amino acid substitution at a particular position is provided. The absence of the nonstandard amino acid substitution at the particular position disrupts one or any combination of translation, folding and function of the essential polypeptide, and the cell dies or experiences reduced or no proliferation if one or more of translation, folding or function of the essential polypeptide is disrupted. In certain aspects, one or more standard amino acid substitutions are present in the essential polypeptide to accommodate the nonstandard amino acid substitution and maintain one or both of proper folding and proper function of the essential polypeptide. In other aspects, the essential polypeptide has been computationally (e.g., with software such as Rosetta) or empirically redesigned (e.g. by random mutagenesis and selection, by targeted mutagenesis and selection and/or computational design) so that the essential polypeptide can no longer fold properly, function properly or both, when the essential polypeptide expresses a standard amino acid at the particular position. In certain aspects, the essential nucleic acid sequence is a gene or encodes an essential polypeptide that is essential for survival, growth, or proliferation. In other aspects, the essential polypeptide is conditionally essential under specific environmental or growth conditions. In other aspects, the conditionally essential polypeptide confers antibiotic resistance or is another selection marker. In still other aspects, the recombinant cell is selected from the group consisting of a prokaryotic cell, a eukaryotic cell, a yeast cell, a bacterium, an archaeal cell, a virion, a virosome, a virus-like particle, a plant cell, an animal cell, an insect cell and a mammalian cell.

In certain exemplary embodiments, a recombinant cell including one or more toxins or toxic substances that are inactive when a nonstandard amino acid is present in the one or more toxins or toxic substances at a particular position is provided. The one or more toxins or toxic substances are activated when the nonstandard amino acid is not present at the particular position, and the activated toxins or toxic substances kill the recombinant cell or prevent or reduce proliferation of the recombinant cell. In certain aspects, one or both of folding and function of the one or more toxins or toxic substances are disrupted when the one or more toxins or toxic substances includes the nonstandard amino acid at the particular position. In certain aspects, the one or more toxins or toxic substances are selected from the group consisting of one or any combination of barnase, Ccdb, Hok, Fst, ParE, MazF, Kid, ToxN, RelE, Doc, HipA and Mvpt. In certain aspects, the recombinant cell has multiple copies of a nucleic acid sequence encoding the one or more toxins or toxic substances. In yet other aspects, the cell is selected from the group consisting of prokaryotic cell, a eukaryotic cell, a yeast cell, a bacterium, an archaeal cell, a virion, a virosome, a virus-like particle, a plant cell, an animal cell, an insect cell and a mammalian cell.

In certain exemplary embodiments, a recombinant cell including an essential polypeptide producing or conferring susceptibility to one or more toxins or toxic substances that are inactive when a nonstandard amino acid is present in the essential polypeptide at a particular position is provided. The essential polypeptide is activated when the nonstandard amino acid is not present at the particular position, and the activated essential polypeptide confers susceptibility to the one or more toxins or toxic substances, which kills the recombinant cell or prevents or reduces proliferation of the recombinant cell. In certain aspects, one or both of folding and function of the essential polypeptide are disrupted when the essential polypeptide includes a nonstandard amino acid at the particular position. In other aspects, the essential polypeptide produces or confers susceptibility to one or more toxins or toxic substances under specific environmental or growth conditions. In certain aspects, the essential polypeptide is selected from the group consisting of one or any combination of sacB tdk, galK, thyA, tolC, tetA, rpsL, and herpes simplex virus thymidine kinase. In yet other aspects, multiple copies of a nucleic acid sequence encoding the essential polypeptide are present in the recombinant cell. In yet other aspects, the cell is selected from the group consisting of prokaryotic cell, a eukaryotic cell, a yeast cell, a bacterium, an archaeal cell, a virion, a virosome, a virus-like particle, a plant cell, an animal cell, an insect cell and a mammalian cell.

In certain exemplary embodiments, a recombinant cell is provided including an essential polypeptide encoded by an essential nucleic acid sequence, said essential polypeptide having a nonstandard amino acid substitution, wherein the absence of the nonstandard amino acid substitution disrupts one or any combination of translation, folding and function of the essential polypeptide. The recombinant cell also includes one or more toxins or toxic substances that are inactive when a nonstandard amino acid is present in the one or more toxins or toxic substances at a particular position, wherein the one or more toxins or toxic substances are activated when the nonstandard amino acid is not present at its particular position, and wherein the activated toxins or toxic substances kill the recombinant cell or prevent or reduce proliferation of the recombinant cell. In certain aspects, the cell dies or experiences reduced or no proliferation if one or more of translation, folding or function is disrupted. In yet other aspects, the cell is selected from the group consisting of prokaryotic cell, a eukaryotic cell, a yeast cell, a bacterium, an archaeal cell, a virion, a virosome, a virus-like particle, a plant cell, an animal cell, an insect cell and a mammalian cell.

In certain exemplary embodiments, a recombinant cell is provided including an essential polypeptide encoded by an essential nucleic acid sequence, said essential polypeptide having a nonstandard amino acid substitution, wherein the absence of the nonstandard amino acid substitution disrupts one or any combination of translation, folding and function of the essential polypeptide. The recombinant cell also includes an essential polypeptide producing or conferring susceptibility to one or more toxins or toxic substances that are inactive when a nonstandard amino acid is present in the essential polypeptide at a particular position, wherein the essential polypeptide is activated when the nonstandard amino acid is not present at the particular position, and wherein the activated essential polypeptide confers susceptibility to the one or more toxins or toxic substances, which kills the recombinant cell or prevents or reduces proliferation of the recombinant cell. In yet other aspects, the cell is selected from the group consisting of prokaryotic cell, a eukaryotic cell, a yeast cell, a bacterium, an archaeal cell, a virion, a virosome, a virus-like particle, a plant cell, an animal cell, an insect cell and a mammalian cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which:

FIG. 14 depicts the range of escape frequencies of the top strains. ( )=mutS+ interpolated by mutS−/100.

FIG. 16 depicts a table summarizing NSAAs suitable for use according to certain exemplary embodiments of the invention. Id.

DETAILED DESCRIPTION OF CERTAIN EXEMPLARY EMBODIMENTS

Figure 1:
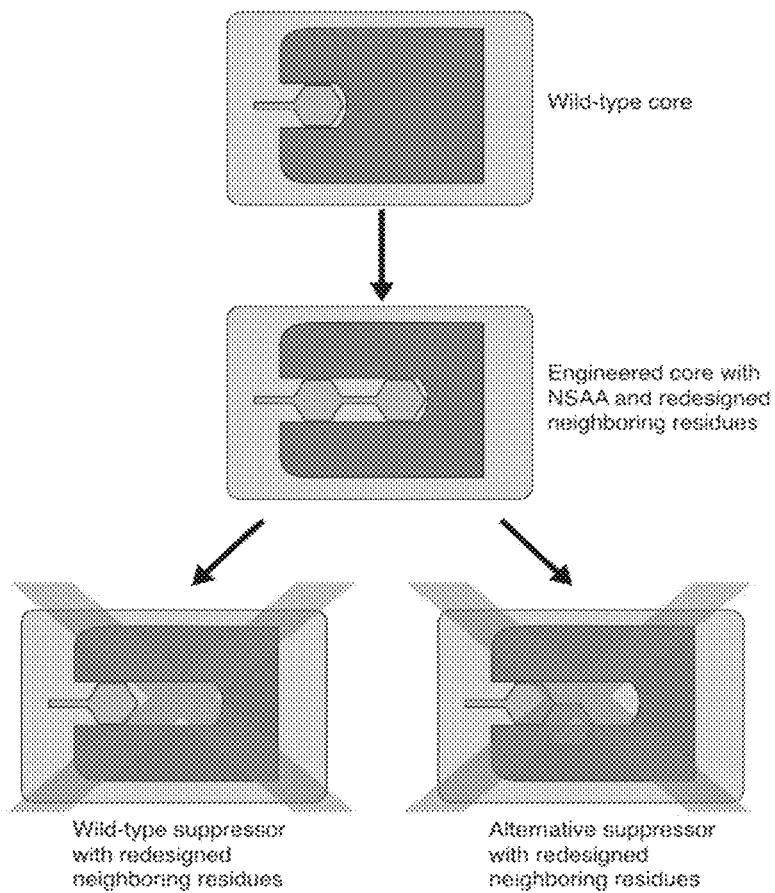
FIG. 1 schematically depicts positive selection for persistent dependence on NSAA incorporation for genetically modified organism viability. (Top panel): Wild-type core of essential protein (grey) with a natural amino acid to be reassigned (orange) and wild-type neighboring amino acid residues (green). (Middle panel): Natural amino acid is reassigned to an NSAA by genomic recoding while the neighboring residues are redesigned to other natural amino acids that exclusively accommodate the NSAA. (Bottom panel): Suppressor mutations to recoded gene or tRNAs result in inviable cells due to misfolding of the essential protein when the suppressor amino acid is too small, leaving a cavity in the protein core (lower left), or has the incorrect geometry, causing steric clashing with the core backbone or side-chains (lower right). Likewise, suppressors that introduce polar or charged amino acids into the hydrophobic core are likely to result in misfolded and/or non-functioning protein, blocking cell viability.
Figure 2:
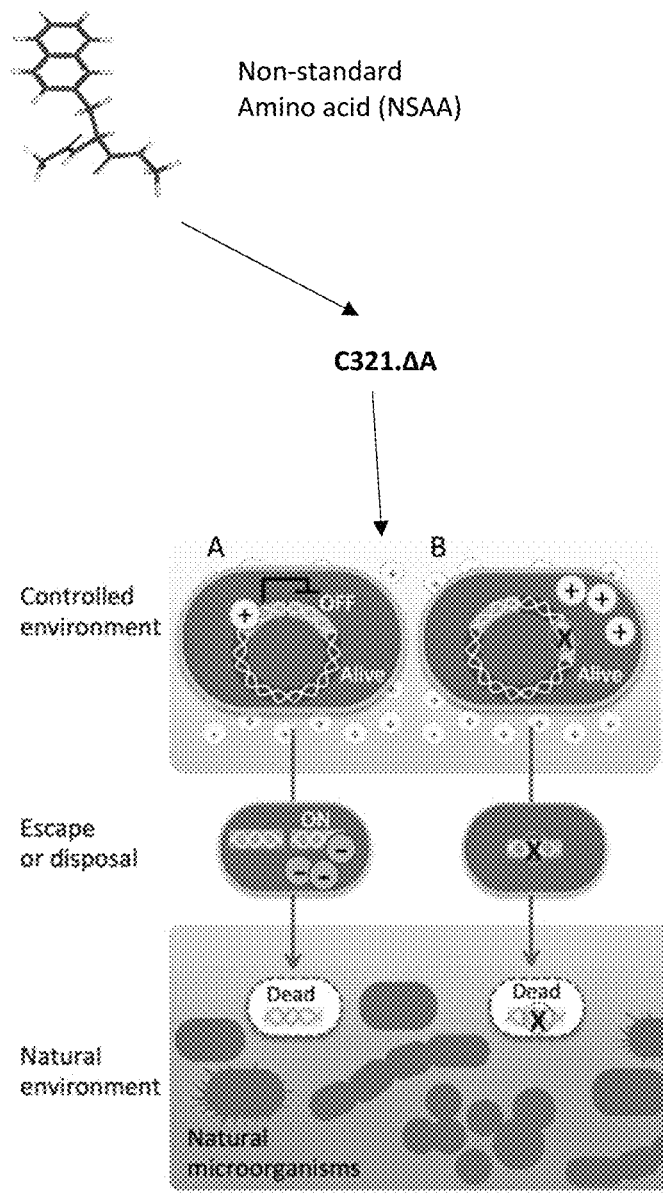
FIG. 2 schematically depicts a synthetic auxotrophy approach according to certain embodiments. Panel A shows a toxin that is inactive in the presence of the intended NSAA (+ symbols) at selected positions. Incorporation of any standard amino acid (− symbols) at the selected position due to suppression or mutagenesis leads to death of the organism. Panel B shows an essential gene that requires the intended NSAA to function. Withdrawal of the intended NSAA leads to death of the organism.

The subject application provides novel recombinant cells and organisms persistently expressing nonstandard amino acids (NSAAs) and methods of making novel recombinant cells and organisms persistently expressing NSAAs.

As used herein, the term "amino acid" includes organic compounds containing both a basic amino group and an acidic carboxyl group. Included within this term are natural amino acids (e.g., L-amino acids), modified and unusual amino acids (e.g., D-amino acids and -amino acids), as well as amino acids which are known to occur biologically in free or combined form but usually do not occur in proteins.

As used herein, the term "NSAA" refers to an unmodified amino acid that is not one of the 20 L-amino acids that typically naturally occur in proteins on Earth and includes alanine, arginine, asparagine, aspartic acid, cysteine, glutamic acid, glutamine, glycine, histidine, isoleucine, leucine, lysine, methionine, phenylalanine, serine, threonine, tyrosine, tryptophan, proline and valine. NSAAs also refer to natural amino acids that are not used by all organisms (e.g. L-pyrrolysine (B. Hao et al., A new uag-encoded residue in the structure of a methanogen methyltransferase. *Science.* 296:1462) and L-selenocysteine (S. Osawa et al., Recent evidence for evolution of the genetic code. *Microbiol. Mol. Biol. Rev.* 56:229)). NSAAs are also known in the art as unnatural amino acids (UAAs) and non-canonical amino acids (NCAAs).

NSAAs include, but are not limited to, p-Acetylphenylalanine, m-Acetylphenylalanine, O-allyltyrosine, Phenylselenocysteine, p-Propargyloxyphenylalanine, p-Azidophenylalanine, p-Boronophenylalanine, O-methyltyrosine, p-Aminophenylalanine, p-Cyanophenylalanine, m-Cyanophenylalanine, p-Fluorophenylalanine, p-Iodophenylalanine, p-Bromophenylalanine, p-Nitrophenylalanine, L-DOPA, 3-Aminotyrosine, 3-Iodotyrosine, p-Isopropylphenylalanine, 3-(2-Naphthyl)alanine, biphenylalanine, homoglutamine, D-tyrosine, p-Hydroxyphenyllactic acid, 2-Aminocaprylic acid, bipyridylalanine, HQ-alanine, p-Benzoylphenylalanine, o-Nitrobenzylcysteine, o-Nitrobenzylserine, 4,5-Dimethoxy-2-Nitrobenzylserine, o-Nitrobenzyllysine, o-Nitrobenzyltyrosine, 2-Nitrophenylalanine, dansylalanine, p-Carboxymethylphenylalanine, 3-Nitrotyrosine, sulfotyrosine, acetyllysine, methylhistidine, 2-Aminononanoic acid, 2-Aminodecanoic acid, pyrrolysine, Cbz-lysine, Boc-lysine, allyloxycarbonyllysine, arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5,-triiodothyronine, and 3,3',5,5'-tetraiodothyronine. Modified or unusual amino acids include D-amino acids, hydroxylysine, 4-hydroxyproline, N-Cbz-protected amino acids, 2,4-diaminobutyric acid, homoarginine, norleucine, N-methylaminobutyric acid, naphthylalanine, phenylglycine, -phenylproline, tert-leucine, 4-aminocyclohexylalanine, N-methyl-norleucine, 3,4-dehydroproline, N,N-dimethylaminoglycine, N-methyl-aminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid, any of the compounds disclose at FIG. 15, FIGS. 16A-16B, FIG. 17, and the like. NSAAs also include amino acids that are functionalized, e.g., alkyne-functionalized, azide-functionalized, ketone-functionalized, aminooxy-functionalized and the like. For reviews of NSAAs and lists of NSAAs suitable for use in certain embodiments of the subject invention, see Liu and Schultz (2010) *Ann. Rev. Biochem.* 79:413, and Kim et al. (2013) *Curr. Opin. Chem. Biol.* 17:412, each of which is incorporated herein by reference in its entirety for all purposes.

In certain aspects, an NSAA of the subject invention has a corresponding aminoacyl tRNA synthetase (aaRS)/tRNA pair. In certain aspects, the aminoacyl tRNA synthetase/tRNA pair is orthogonal to those in a genetically modified organism such as, e.g., a prokaryotic cell, a bacterium (e.g., *E. coli*), a eukaryotic cell, a yeast, a plant cell, an insect cell, a mammalian cell, a virus, etc. In certain aspects, an NSAA of the subject invention is non-toxic when expressed in a genetically modified organism such as, e.g., a prokaryotic cell, a bacterium (e.g., *E. coli*), a eukaryotic cell, a yeast, a plant cell, an insect cell, a mammalian cell, a virus, etc. In certain aspects, an NSAA of the subject invention is not or does not resemble a natural product present in a cell or organism. In certain aspects, an NSAA of the subject invention is hydrophobic, hydrophilic, polar, positively charged, or negatively charged. In other aspects, an NSAA of the subject invention is commercially available (such as, e.g., bipA and L-2-Naphthylalanine (napA)) or synthesized according to published protocols.

As used herein, the term "peptide" includes compounds that consist of two or more amino acids that are linked by means of a peptide bond. Peptides may have a molecular weight of less than 10,000 Daltons, less than 5,000 Daltons, or less than 2,500 Daltons. The term "peptide" also includes compounds containing both peptide and non-peptide components, such as pseudopeptide or peptidomimetic residues or other non-amino acid components. Such compounds containing both peptide and non-peptide components may also be referred to as a "peptide analog."

As used herein, the terms "polypeptide" and "protein" include compounds that consist of amino acids arranged in a linear chain and joined together by peptide bonds between the carboxyl and amino groups of adjacent amino acid residues.

In certain exemplary embodiments, a recombinant cell or recombinant organism of the subject invention comprises an "essential nucleic acid sequence" or "essential gene." In certain aspects, expression of the essential nucleic acid sequence or essential gene produces an "essential polypeptide" or "essential protein." In certain aspects, alternative nucleic acid sequences can encode for the same essential polypeptide. If one or more of translation, proper folding or proper functioning of the essential polypeptide encoded by the essential nucleic acid sequence or essential gene is disrupted, the recombinant cell or recombinant organism dies or experiences reduced or no proliferation. Essential nucleic acid sequences, essential genes, essential polypeptides or essential proteins can be involved with cell growth, cell division, housekeeping, cell death, and the like. Essential nucleic acid sequences, essential genes, essential polypeptides or essential proteins can be conditionally essential (e.g., the ability to survive at high salt concentrations, high heat conditions, during drought, etc.). Non-limiting, exemplary essential nucleic acid sequences and essential genes include, but are not limited to, tyrS, alaS, metS, metG, pgk, adk, holB and the like. Non-limiting, exemplary essential polypeptides and essential proteins include, but are not limited to, TyrS, AlaS, MetS, MetG, Pgk, Adk, HolB and the like. Using the subject disclosure as a guide, one of ordinary skill in the art could readily select additional suitable essential nucleic acid sequences and essential genes for use with the recombinant cells, recombinant organisms and methods described herein.

In certain exemplary embodiments, a recombinant cell or recombinant organism of the subject invention comprises one or more toxins or toxic substances that kill the cell or organism or prevent or reduce its proliferation. Non-limiting, exemplary toxins and toxic substances include, but are not limited to, Ccdb, Hok, Fst, ParE, MazF, Kid, ToxN, RelE, Doc, HipA, Mvpt, SacB Tdk, GalK, ThyA, TolC, TetA, RpsL, barnase, and herpes simplex virus thymidine kinase. Using the subject disclosure as a guide, one of ordinary skill in the art could readily select additional suitable toxins and toxic substances for use with the recombinant cells, recombinant organisms and methods described herein.

In certain exemplary embodiments, a genomically recoded organism comprising: a first essential polypeptide encoded by a first essential gene, said first essential polypeptide having a first nonstandard amino acid substitution, wherein the absence of the first nonstandard amino acid substitution disrupts one or both of folding and function of the first essential polypeptide; and a second essential gene encoding a premature stop codon, wherein the presence of a second nonstandard amino suppresses the premature stop codon and allows translation of a second essential polypeptide is provided. In certain aspects, the organism comprises two or more stop codons. In certain aspects, the organism further comprises one or more standard amino acid substitutions in the first essential polypeptide to accommodate the nonstandard amino acid substitution and maintain one or both of proper folding and proper function of the first essential polypeptide. In certain aspects, the nonstandard amino acids are one or both of L-4,4'-Biphenylalanine and L-2-Naphthylalanine. In certain aspects, the first essential polypeptide is the same or is different than the second essential polypeptide. In certain aspects, the nonstandard amino acid in the first essential polypeptide is the same or different than the nonstandard amino acid in the second essential polypeptide. In certain aspects, the organism expresses a plurality of nonstandard amino acids. In other aspects, one or both of the first and second essential genes are selected from the group consisting of one or any combination of tyrS, alaS, pgk, metS, metG, adk, and holB. In certain aspects, the organism is weakened or dies if folding of the first essential polypeptide is disrupted, if a function of the first essential polypeptide is disrupted, or if translation of the second essential polypeptide is terminated at the premature stop codon. In still other aspects, the recombinant cell is selected from the group consisting of a prokaryotic cell, a eukaryotic cell, a yeast cell, a bacterium, an archaeal cell, a virion, a virosome, a virus-like particle, a plant cell, an animal cell, an insect cell and a mammalian cell.

In certain exemplary embodiments, a genomically recoded organism comprising: 1) a first essential polypeptide encoded by an essential gene, said first essential polypeptide having a first nonstandard amino acid substitution, wherein the absence of the first nonstandard amino acid substitution disrupts one or both of folding and function of the first essential polypeptide; 2) an essential gene encoding a premature stop codon, wherein the presence of a second nonstandard amino suppresses the premature stop codon and allows translation of a second essential polypeptide; and 3) a toxin that is inactive when a nonstandard amino acid is present in the toxin at a particular position, wherein the toxin is activated when the nonstandard amino acid is not present at the particular position, and wherein the activated toxin kills the organism. In certain aspects, the organism is weakened or dies if folding of the first essential polypeptide is disrupted, if a function of the first essential polypeptide is disrupted, or if translation of the second polypeptide is terminated at the premature stop codon. In still other aspects, the recombinant cell is selected from the group consisting of a prokaryotic cell, a eukaryotic cell, a yeast cell, a bacterium, an archaeal cell, a virion, a virosome, a virus-like particle, a plant cell, an animal cell, an insect cell and a mammalian cell.

The term "nucleoside," as used herein, includes the natural nucleosides, including 2'-deoxy and 2'-hydroxyl forms, e.g. as described in Komberg and Baker, DNA Replication, 2nd Ed. (Freeman, San Francisco, 1992). "Analogs" in reference to nucleosides includes synthetic nucleosides having modified base moieties and/or modified sugar moieties, e.g., described by Scheit, Nucleotide Analogs (John Wiley, New York, 1980); Uhlman and Peyman, Chemical Reviews, 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al., *Exp. Opin. Ther. Patents*, 6: 855-870 (1996); Mesmaeker et al., *Current Opinion in Structural Biology*, 5:343-355 (1995); and the like. Exemplary types of polynucleotides that are capable of enhancing duplex stability include oligonucleotide phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Oligonucleotide" or "polynucleotide," which are used synonymously, means a linear polymer of natural or modified nucleosidic monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Usually nucleosidic monomers are linked by phosphodiester bonds. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. It is clear to those skilled in the art when oligonucleotides having natural or non-natural nucleotides may be employed in methods and processes described herein. For example, where processing by an enzyme is called for, usually oligonucleotides consisting solely of natural nucleotides are required. Likewise, where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., *Molecular Cloning*, Second Edition (Cold Spring Harbor Laboratory, New York, 1989), and like references. Oligonucleotides and polynucleotides may be single stranded or double stranded.

Oligonucleotides and polynucleotides may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

Nucleic acid molecules may be isolated from natural sources or purchased from commercial sources. Oligonucleotide sequences may also be prepared by any suitable method, e.g., standard phosphoramidite methods such as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain exemplary embodiments, recombinant cells and/or recombinant organisms are provided that express one or more NSAAs. As used herein, an "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., *Danio rerio*), a worm e.g., a roundworm (e.g., *C. elegans*), a plant, any eukaryote, any transgenic species and any single or multiple cells derived therefrom. An organism or cell further includes, but is not limited to, a yeast (e.g., *S. cerevisiae*) cell, a yeast tetrad, a yeast colony, a bacterium, a bacterial colony, an archaeon, any prokaryote, a virion, a virosome, a virus-like particle, a parasitic microbe, an infectious protein and the like and/or cultures of any of these.

In certain aspects, one or more biological samples are provided from one or more recombinant organisms or one or more recombinant cells. As used herein, a "biological sample" may be a single cell or many cells. A biological sample may comprise a single cell type or a combination of two or more cell types. A biological sample further includes a collection of cells that perform a similar function such as those found, for example, in a tissue. As used herein, a tissue includes, but is not limited to, epithelial tissue (e.g., skin, the lining of glands, bowel, skin and organs such as the liver, lung, kidney), endothelium (e.g., the lining of blood and lymphatic vessels), mesothelium (e.g., the lining of pleural, peritoneal and pericardial spaces), mesenchyme (e.g., cells filling the spaces between the organs, including fat, muscle, bone, cartilage and tendon cells), blood cells (e.g., red and white blood cells), neurons, germ cells (e.g., spermatozoa, oocytes), amniotic fluid cells, placenta, stem cells and the like. A tissue sample includes microscopic samples as well as macroscopic samples. In certain aspects, a biological sample is peripheral blood. In other aspects, a biological sample is a fluid such as saliva, synovial fluid, or the like. In still other aspects, a biological sample is from one or more cell cultures, tissue sections and/or biopsies.

Isolation, extraction or derivation of nucleic acid sequences may be carried out by any suitable method. Isolating nucleic acid sequences from a biological sample generally includes treating a biological sample in such a manner that nucleic acid sequences present in the sample are extracted and made available for analysis. Any isolation method that results in extracted nucleic acid sequences may be used in the practice of the present invention. It will be understood that the particular method used to extract nucleic acid sequences will depend on the nature of the source.

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, $2^{nd}$ Ed., Cold Spring Harbour Laboratory Press: New York, N.Y.). Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (see, for example, J. Sambrook et al., "Molecular Cloning: A Laboratory Manual" 1989, $2^{nd}$ Ed., Cold Spring Harbour Laboratory Press: New York) and several kits for RNA extraction from bodily fluids are commercially available (e.g., Ambion, Inc. (Austin, Tex.); Amersham Biosciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif.)).

Certain embodiments of the subject invention are directed to a first nucleic acid or polypeptide sequence having a certain sequence identity or percent homology to a second nucleic acid or polypeptide sequence, respectively.

Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov (1986) *Nucl. Acids Res.* 14:6745. An exemplary implementation of this algorithm to determine percent identity of a sequence is provided by the Genetics Computer Group (Madison, Wis.) in the "BestFit" utility application. The default parameters for this method are described in the *Wisconsin Sequence Analysis Package Program Manual*, Version 8 (1995) (available from Genetics Computer Group, Madison, Wis.).

One method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the NCBI/NLM web site.

Alternatively, homology can be determined by hybridization of polynucleotides under conditions that form stable duplexes between homologous regions, followed by digestion with single-stranded-specific nuclease(s), and size determination of the digested fragments. Two DNA sequences, or two polypeptide sequences are "substantially homologous" to each other when the sequences exhibit at least about 80%-85%, at least about 85%-90%, at least about 90%-95%, or at least about 95%-98%, or about 95%, about 96%, about 97%, about 98%, or about 99% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *Molecular Cloning: A Laboratory Manual*, Second Edition, (1989) Cold Spring Harbor, N.Y.; *Nucleic Acid Hybridization: A Practical Approach*, editors B. D. Hames and S. J. Higgins, (1985) Oxford; Washington, D.C.; IRL Press.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization, supra).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as varying wash conditions. The selection of a particular set of hybridization conditions is selected following standard methods in the art (see, for example, Sambrook et al., supra).

As used herein, the term "hybridizes under stringent conditions" is intended to describe conditions for hybridization and washing under which nucleotide sequences at least 60% identical to each other typically remain hybridized to each other. In one aspect, the conditions are such that sequences at least about 70%, at least about 80%, at least about 85% or 90% or more identical to each other typically remain hybridized to each other. Such stringent conditions are known to those skilled in the art and can be found in *Current Protocols in Molecular Biology*, John Wiley & Sons, N.Y. (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50° C., at 55° C., or at 60° C. or 65° C.

In certain exemplary embodiments, methods for amplifying nucleic acid sequences are provided. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self-sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277: 7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, PCR: *A Practical Approach* and *PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.*, 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques*, 26:112-126 (1999); Becker-Andre et al., *Nucleic Acids Research*, 17:9437-9447 (1989); Zimmerman et al., *Biotechniques*, 21:268-279 (1996); Diviacco et al., *Gene*, 122:3013-3020 (1992); Becker-Andre et al., *Nucleic Acids Research*, 17:9437-9446 (1989); and the like.

In certain exemplary embodiments, methods of determining the sequence identities of nucleic acid sequences are provided. Determination of the sequence of a nucleic acid sequence of interest (e.g., immune cell nucleic acid sequences) can be performed using variety of sequencing methods known in the art including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511,803, and PCT/US05/

06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa, ABI-SOLiD, ION Torrents, Complete Genomics, Pacific Bioscience, Helicos, Polonator platforms (Worldwide Web Site: Polonator.org), and the like, can also be utilized. High-throughput sequencing methods are described in U.S. Ser. No. 61/162,913, filed Mar. 24, 2009. A variety of light-based sequencing technologies are known in the art (Landegren et al. (1998) *Genome Res.* 8:769-76; Kwok (2000) *Pharmocogenomics* 1:95-100; and Shi (2001) *Clin. Chem.* 47:164-172).

Embodiments of the invention include the use of computer software to computationally design and/or analyze nucleic acid sequences and/or polypeptides described herein. Such software may be used in conjunction with individuals performing design and/or analysis by hand or in a semi-automated fashion or combined with an automated system. In at least some embodiments, the gene/oligonucleotide design/analysis software is implemented in a program written in the JAVA programming language. The program may be compiled into an executable that may then be run from a command prompt in the WINDOWS XP operating system. The invention is similarly not limited to implementation using a specific software code, programming language, operating system environment or hardware platform. In certain aspects, protein design may be performed using Rosetta software. (See, e.g., U.S. Pat. No. 8,340,951, incorporated herein by reference in its entirety for all purposes.)

The following examples are set forth as being representative of the present invention. These examples are not to be construed as limiting the scope of the invention as these and other equivalent embodiments will be apparent in view of the present disclosure, figures and accompanying claims.

EXAMPLE I

Positive and Negative Selection Strategies

According to certain exemplary embodiments, genetically modified organisms were provided and maintained using a positive selection for NSAA incorporation. NSAA-dependent genetically modified organisms were engineered by reassigning the UAG codon to incorporate an NSAA at either N-terminal or solvent-exposed positions in essential genes. Since these positions are subject to suppression by standard amino acids, this approach has been extended to engineer essential genes that require the NSAA for folding and/or function in addition to translation. A computational second-site suppressor strategy (T. Kortemme et al. (2004) Computational redesign of protein-protein interaction specificity. *Nat. Struct. Mol. Biol.* 11:371) was employed to redesign the hydrophobic cores of essential genes in this fashion. This approach mutated core positions in essential genes to an NSAA, and then redesigned the neighboring amino acid residues to exclusively accommodate the introduced NSAA. Suppression of the NSAA then disrupted folding and/or function of the essential protein. This strategy was applied to the core positions of all essential genes in *E. coli* with available X-ray structures (141 genes) using L-4,4'-biphenylalanine as the NSAA. NSAA dependence was assayed in strains with redesigned essential genes including tyrS, alaS, holB, metG, pgk and adk.

In certain exemplary embodiments, genetically modified organisms are provided and maintained using a negative selection for NSAA incorporation. Mutations to endogenous or engineered tRNAs can produce suppressors that incorporate natural amino acids at recoded positions, compromising safety features that rely on recoding. In order to select against suppressors arising, natural toxins are engineered with folding and/or function that is disrupted only when an NSAA is incorporated at recoded positions. Incorporation of a natural amino acid at a recoded position then activates the toxin and kills the cell. Since certain positions may be amenable to excluding some but not all natural amino acids, this strategy is applied across multiple positions and toxins, including barnase, ccdb, hok, fst, parE, mazF, kid, toxN, relE, doc, hipA and mvpt. Multiple copies may be included to mitigate loss of the toxin genes via mutational inactivation, deletion, or the like.

EXAMPLE II

Protein Design Using Second-Site Strategy

Figure 3:
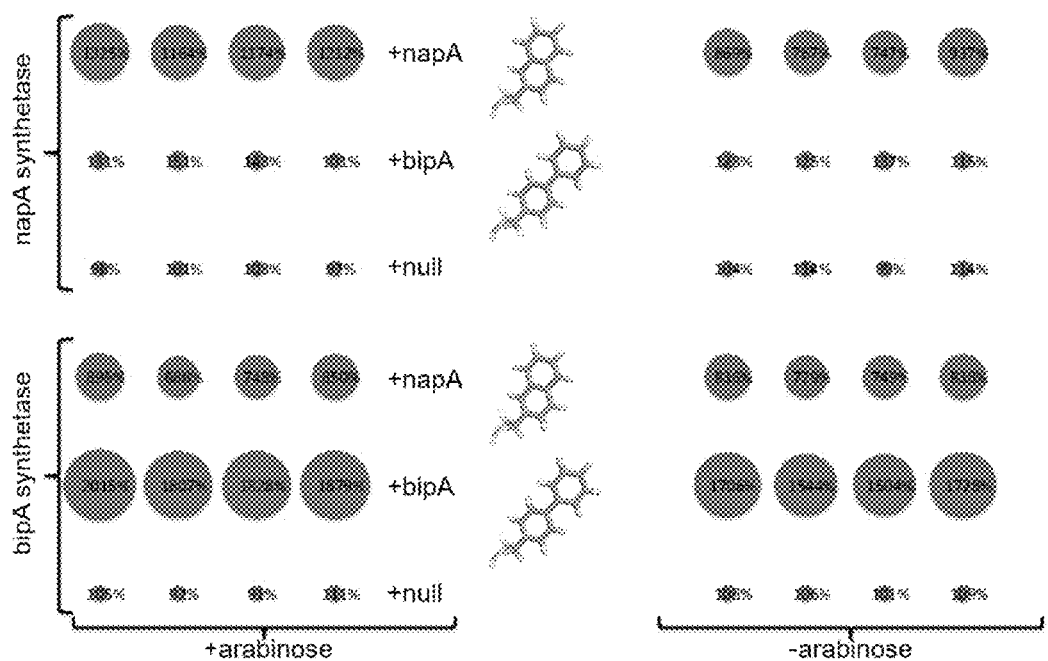
FIG. 3 depicts a green fluorescent protein 1-UAG (stop codon) assay in which the specificities of the L-4,4'-Biphenylalanine (bipA) and L-3-(2-Naphthyl)alanine (napA) aminoacyl tRNA synthetases for their cognate NSAAs were assayed.
Figure 4:
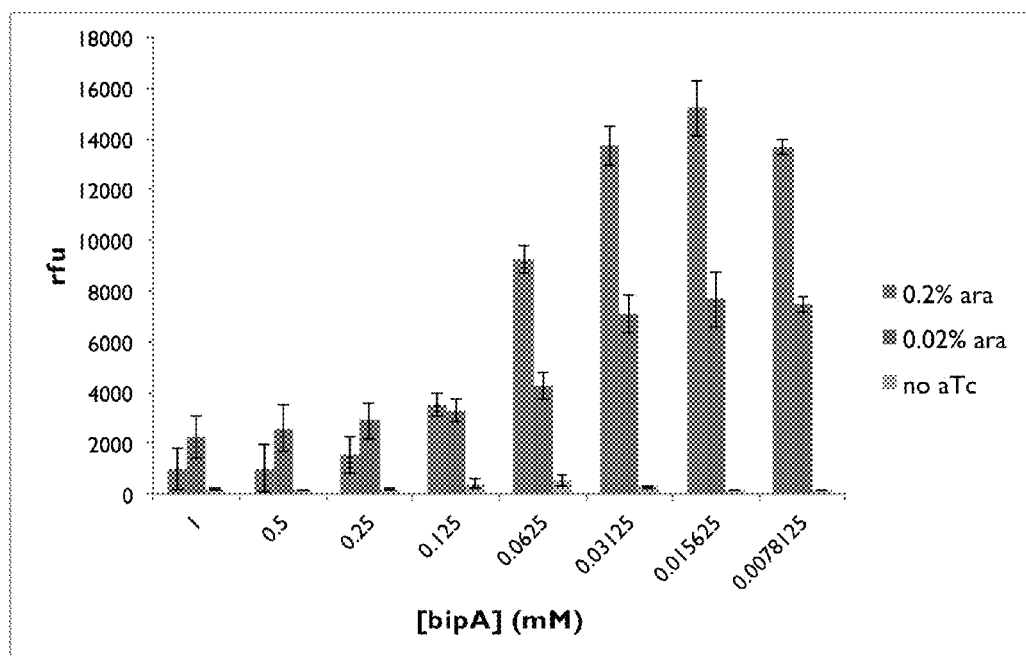
FIG. 4 graphically depicts optimization of L-4,4'-Biphenylalanine (bipA) and arabinose (ara) concentrations for the expression of GFP (fluorescence, induced by anhydrotetracycline (aTc)).

Plasmids were assembled containing the aaRS and tRNA for bipA and napA (2 copies each, one constitutive, one under arabinose-inducible transcriptional control). Incorporation and specificity were assayed using a GFP with 1 UAG codon (FIG. 3). The assay indicated high activity for the cognate NSAA and high specificity (low misincorporation of standard amino acids).

Rosetta was used to apply the second-site suppressor strategy to reengineer essential proteins to exclusively accommodate bipA and napA at certain positions. A set of 129 high-resolution (2.8 Å) X-ray structures of essential *E. coli* proteins was compiled. The solvent accessible surface area (SASA) of all residues in all proteins was computed, and 13,564 "buried" residues were identified. All buried positions were redesigned to incorporate an NSAA. Neighbors were redesigned to accommodate an NSAA. Best candidates were identified by selecting redesigned protein cores that were tightly packed around the NSAA, which were thus predicted to be destabilized in the presence of any standard amino acid. It was determined that the target site was not proximal to residues critical for catalysis, substrate binding, or allosteric transduction. It was determined that the same product or a similar product was not found in nature. Best candidates were refined with another round of design with manually selected degrees of freedom.

Design protocols resulted in six essential polypeptides that were pursued further experimentally. BipA simulations produced more promising designs. Without intending to be bound by scientific theory, this was likely due to the presence of more conformations because of the extra rotatable bond, and/or due to difficulties in suppression due to larger cavity formed. The six bipA target systems were as follows: 1) adenylate kinase (adk) (an essential enzyme required for the biosynthesis of purine ribonucleotides); 2) alanyl-tRNA synthetase (alaS); 3) DNA polymerase III subunit delta (holB); 4) methionyl-tRNA synthetase (metG); 5) phosphoglycerate kinase (pgk) (produces 3-Phosphoglyceric acid, a metabolic intermediate in glycolysis); and 6) tyrosyl-tRNA synthetase (tyrS).

Targets were scattered across the genome, so that multiple redesigns made gene transfer difficult. Out of 4.6 MB, the genomic position of each of the six essential polypeptides was as follows: adk: 496,399→497,043; alaS: 2,817,403←2,820,033; holB: 1,154,985→1,155,989; metG: 2,192,322→2,194,355; pgk: 3,069,481←3,070,644; and tyrS: 1,713,972←1,715,246. (Numbers represent left and right genome positions of the gene; arrows represent orientation of the gene (→ is a gene transcribed on the + strand; ← is a gene transcribed on the − strand).)

EXAMPLE III

Two Methods for Designing Strains

Figure 5:
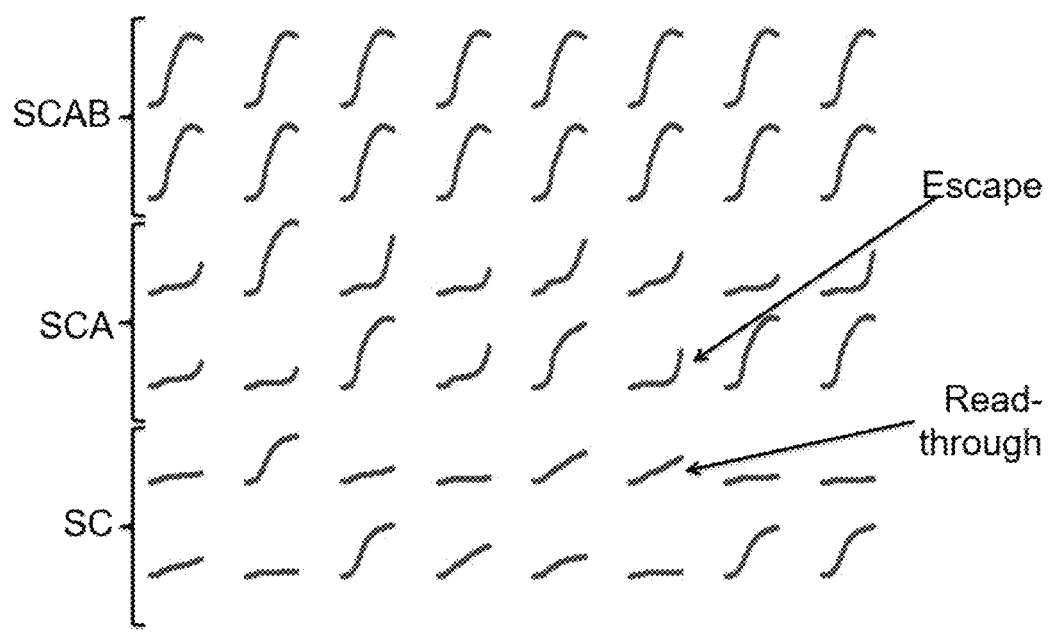
FIG. 5 schematically depicts adk strain results. Examples of escape (i.e., mutations conferring the ability to grow in the absence of bipA) and read-through (i.e., the strain is not fully dependent on bipA incorporation for survival) are indicated. SCAB refers to LB-Lennox media supplemented with sodium dodecyl sulphate (SDS), chloramphenicol (Cm), arabinose (ara), and bipA. SCA refers to LB-Lennox media supplemented with SDS, Cm, and arabinose. SC refers to LB-Lennox media supplemented with SDS and Cm.

Designed strains were constructed in two ways:
Fewer Compensatory Mutations (all Targets)
1. Encoded desired mutations on degenerate oligos
2. Introduced tolC cassette near target gene using lambda red recombineering
3. Inactivated tolC using lambda red recombineering
4. Introduced oligos to mutate the essential gene and to reactivate tolC using lambda red recombineering
5. Replica plated with/without bipA to identify bipA-dependent clones
6. Phenotypic (bipA dependence) and genotypic (PCR and sequencing) screening of recombinants More Compensatory Mutations (Adk, tyrS)
1. Encoded desired mutations in degenerate IDT gBlocks (500 bp synthetic double-stranded DNA constructs)
2. Assembled into full genes using isothermal assembly and/or PCR assembly
3. Inserted a copy of wild type essential gene at tolC locus by using lambda red recombineering
4. Deleted essential gene locus with tolC by using lambda red recombineering
5. Replaced tolC in wild type locus with redesigned essential gene by using lambda red recombineering
6. Deleted redundant copy of wild type essential gene by using lambda red recombineering to reintroduce tolC into tolC locus
7. Phenotypic (bipA dependence) and genotypic (PCR and sequencing) screening of recombinants Candidates showed different levels of dependence and different escape mechanisms (FIG. 5). Without intending to be bound by scientific theory, there were several reasons for growth in the absence of bipA. "Read through" or "bleed through," in which near-cognate suppression by natural tRNAs incorporating natural amino acids resulted in adequate expression and function of the essential polypeptide. Escape suppressors: mutations in the redesigned essential polypeptide relieving bipA dependence, mutations in natural tRNAs conferring the ability to incorporate natural amino acids at the UAG codon that are capable of rescuing polypeptide function, or mutations in the bipA aaRS and/or tRNA allowing them to recognize natural tRNAs or natural amino acids.

"Ideal" compensatory second-site mutations should prevent both "bleed through" and "escape suppressors," which is very challenging. Most strains identified were mutator strains (mismatch repair is inactivated, leading to a 100-fold increase in mutation frequency). This increased mutation load allowed detection of rare escape mechanisms, but escape frequencies could be reduced approximately 100-fold by reintroducing mismatch repair. Synthetase and tRNA were on a 10-20 copy plasmid or in single copy on the genome.

EXAMPLE IV

Genomically Recoded Strain Analysis

Figure 6:
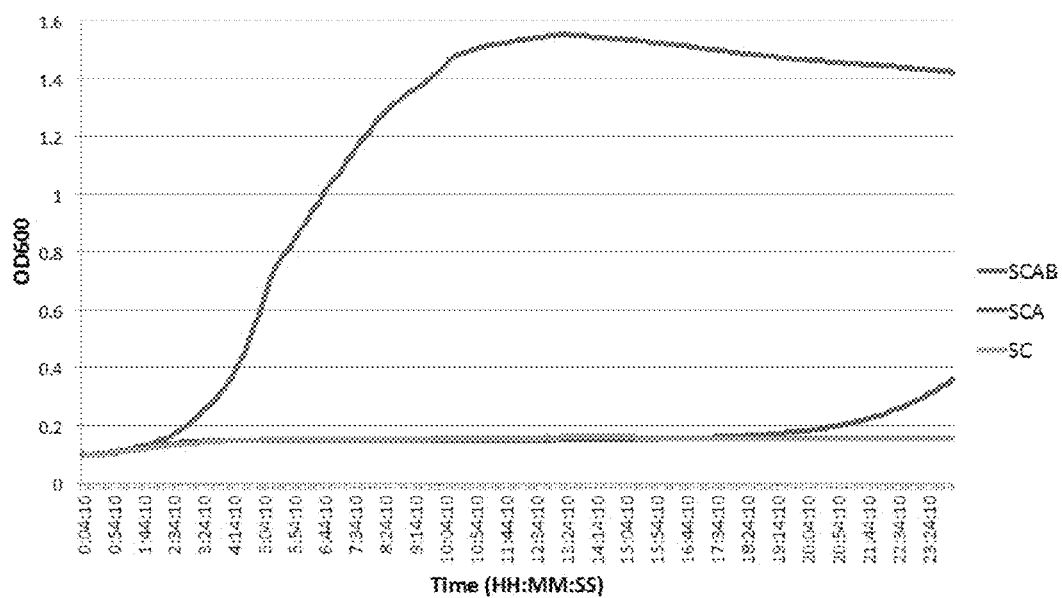
FIG. 6 graphically depicts the results of a growth assay of E. coli expressing a recoded adenylate kinase (adk). This redesigned adk clone exhibited dependence on bipA for survival, which was eventually overcome by mutational escape.

Adenylate Kinase (Adk)
Adenylate kinase (adk) having the following standard and nonstandard amino acid substitutions was generated: I4A, L6V, V103A, L178bipA, Y182V, T191I. Results of growth assays are depicted at FIG. 6.

Figure 7:
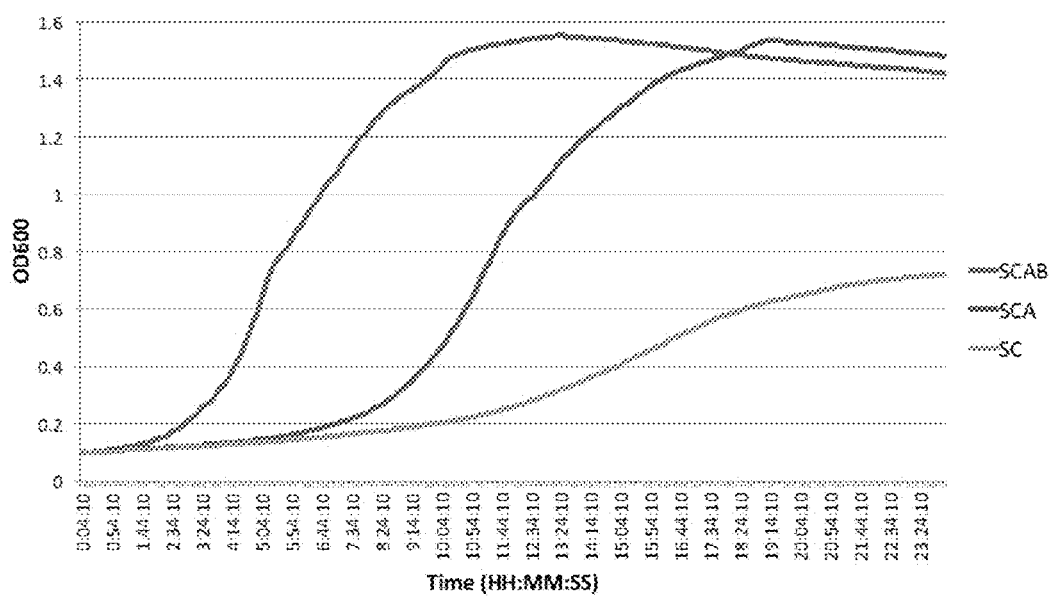
FIG. 7 graphically depicts the results of a growth assay of E. coli expressing a recoded alanyl-tRNA synthetase (alaS). This redesigned alaS clone exhibited dependence on bipA for survival, which was readily overcome by mutational escape.

Alanyl-tRNA Synthetase (alaS)
Alanyl-tRNA synthetase (alaS) having the following standard and nonstandard amino acid substitutions was generated: startUAG, F90A, F293A, L338bipA, M342A, L349P. Results of growth assays are depicted at FIG. 7.

Figure 8:
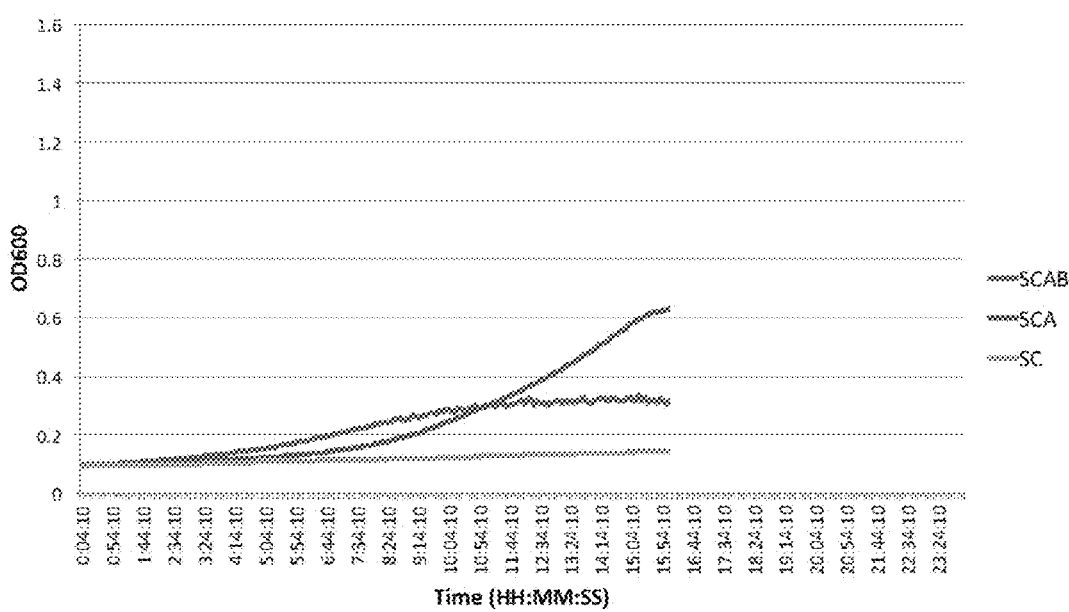
FIG. 8 graphically depicts the results of a growth assay of E. coli expressing a recoded DNA polymerase III subunit delta (holB). This redesigned holB clone exhibited extremely impaired growth and lack of dependence on bipA for survival.
Figure 9:
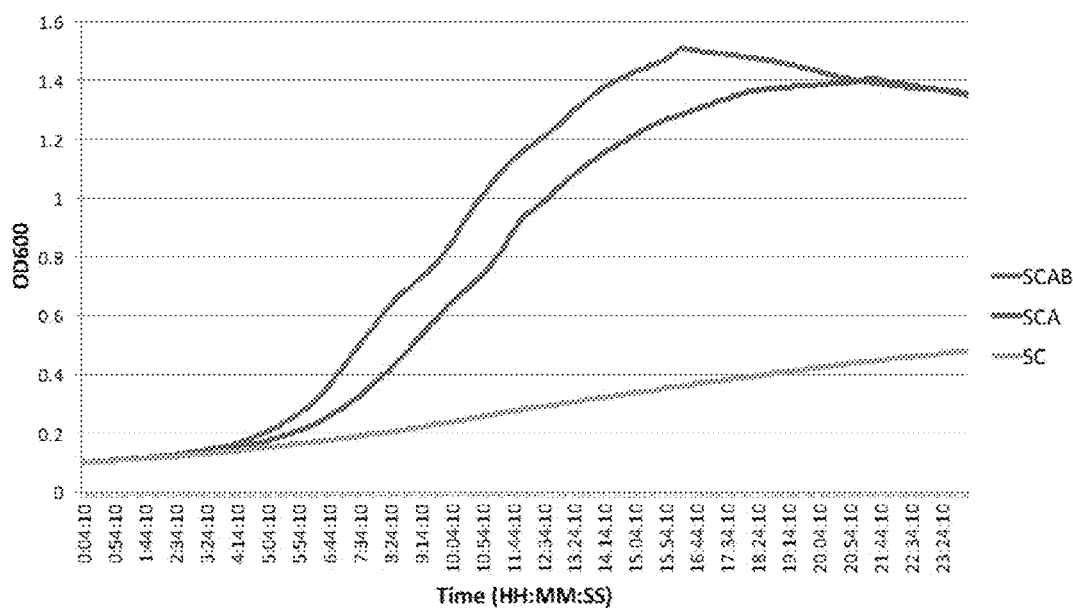
FIG. 9 graphically depicts the results of a growth assay of E. coli expressing a recoded methionyl-tRNA synthetase (metG). This redesigned metG clone exhibited dependence on translation for survival, but incorporation of natural amino acids (in the SCA condition) appeared to rescue fitness.

DNA Polymerase III Subunit Delta (holB)
DNA polymerase III subunit delta (holB) having an A190bipA substitution was generated. Results of growth assays are depicted at FIG. 8. The only successful substitution in holB was UAG. Without intending to be bound by scientific theory, it is possible that recombination frequencies were too low, but it was more likely that the redesign was not compatible with holB folding and/or function Methionyl-tRNA Synthetase (metG)
Methionyl-tRNA synthetase (metG) having the following standard and nonstandard amino acid substitutions was generated: M485A, F502G, L503bipA. Results of growth assays are depicted at FIG. 9.

Figure 10:
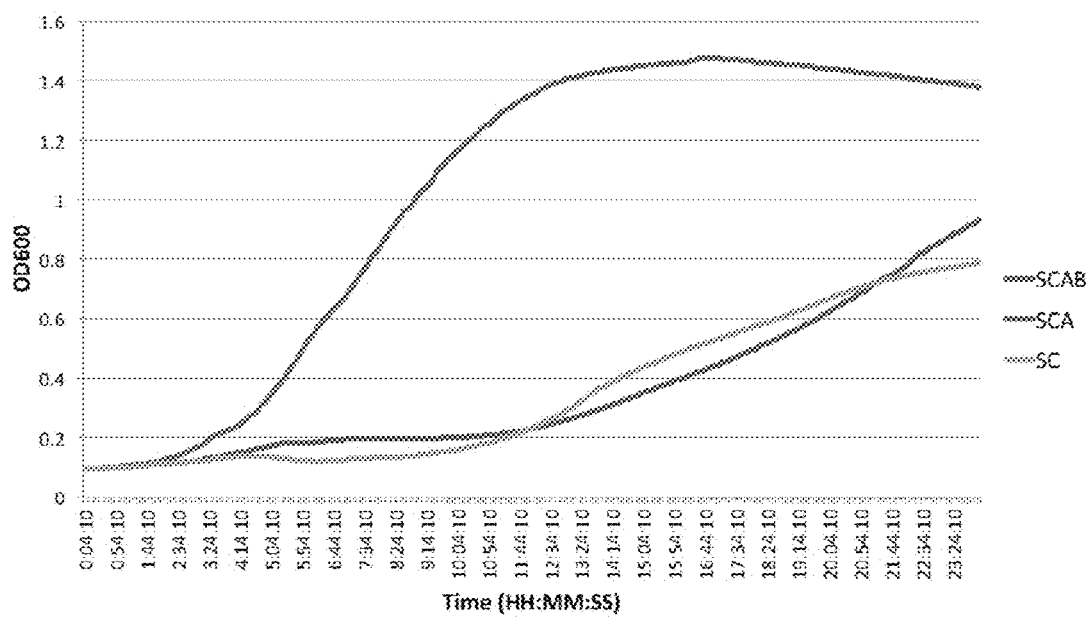
FIG. 10 graphically depicts the results of a growth assay of E. coli expressing a recoded phosphoglycerate kinase (pgk). This redesigned pgk clone exhibited dependence on bipA for survival, which was eventually overcome by mutational escape.
Figure 11:
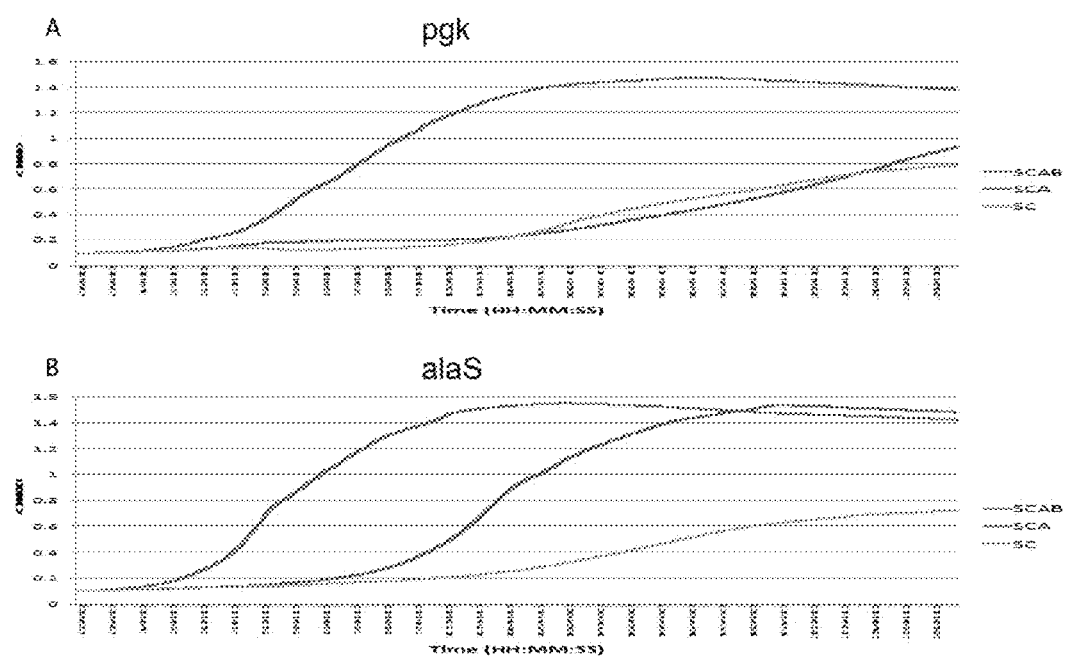
FIG. 11 graphically compares growth assays of E. coli expressing phosphoglycerate kinase (pgk) (top panel, A) and alanyl-tRNA synthetase alaS (bottom panel, B). Without intending to be bound by scientific theory, lack of increased escape rate in the presence of arabinose (SCA condition) suggests an alternative escape mechanism for pgk.

Phosphoglycerate Kinase (Pgk)
Phosphoglycerate kinase (pgk) having the following standard and nonstandard amino acid substitutions was generated: V185A, I187A, I211G, L297bipA. Results of growth assays are depicted at FIG. 10. Phosphoglycerate kinase may have an escape mechanism that is unaffected by bipA aaRS/tRNA expression, as evidenced by equivalent growth profiles in presence and absence of arabinose. See FIG. 11.

Figure 12:
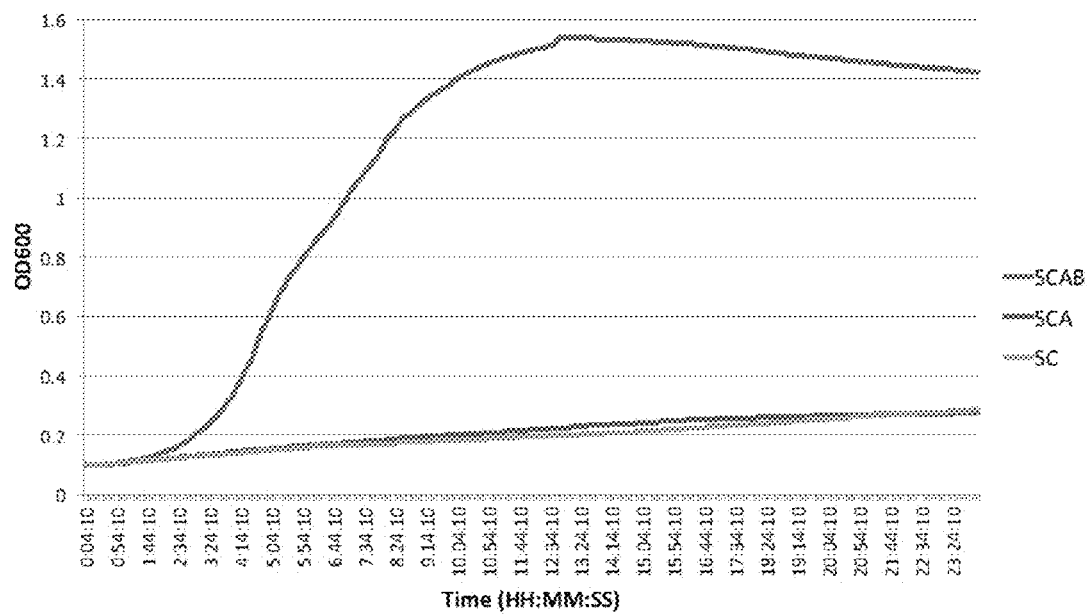
FIG. 12 graphically depicts the results of a growth assay of E. coli expressing a recoded tyrosyl-tRNA synthetase (tyrS). This redesigned tyrS clone exhibited dependence on bipA for survival. No escape was observed after approximately 24 hours.

Tyrosol-tRNA Synthetase (tyrS)
Tyrosyl-tRNA synthetase (tyrS) having the following standard and nonstandard amino acid substitutions was generated: F706A, W778F, T787V, F823G, L907bipA, V919A. Results of growth assays are depicted at FIG. 12.

Figure 13:
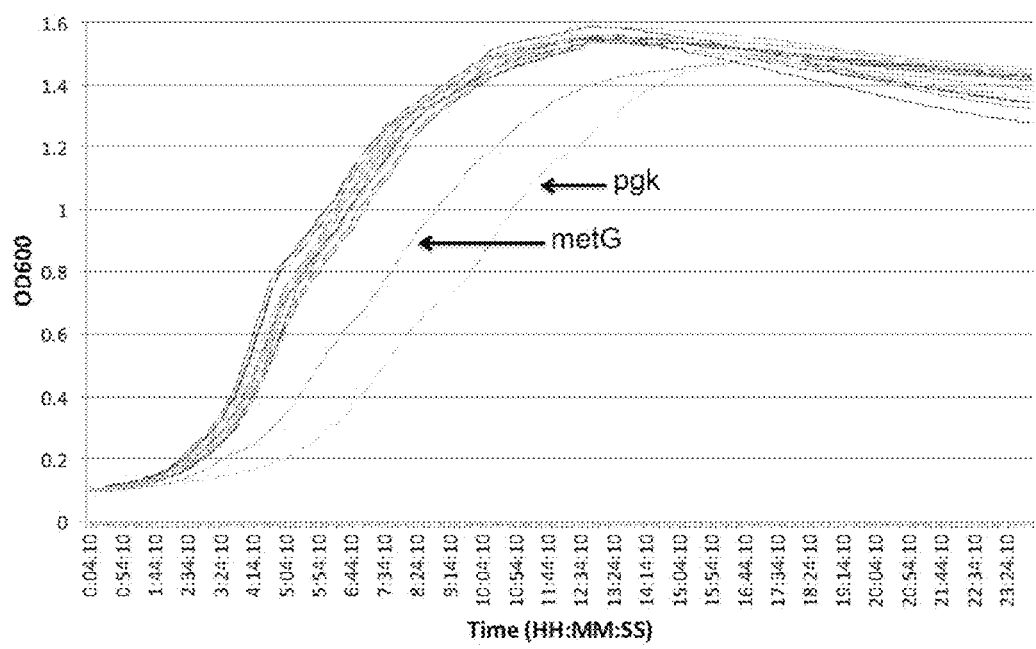
FIG. 13 graphically depicts growth assays of the top strains in the presence of bipA. Most clones exhibited normal growth in the presence of bipA, although pgk (green) and metG (orange) clones exhibited reduced fitness.
Figure 15:
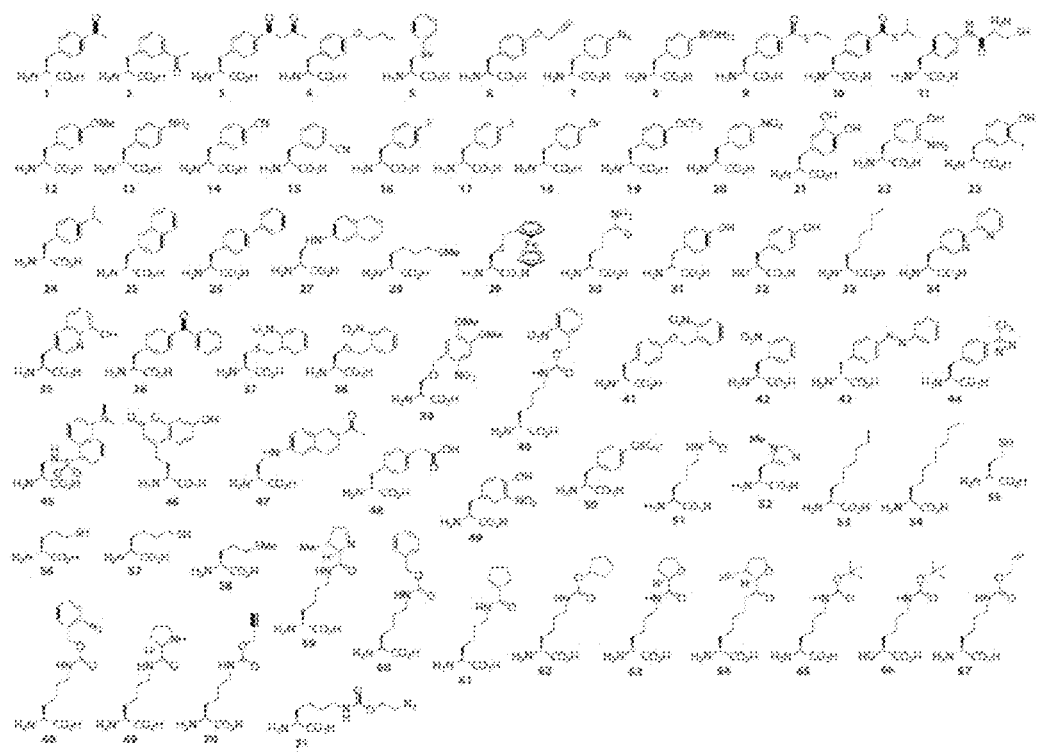
FIG. 15 depicts NSAAs suitable for use according to certain exemplary embodiments of the invention (Liu and Schultz (2010) *Ann. Rev. Biochem.* 79:413).
Figure 17:
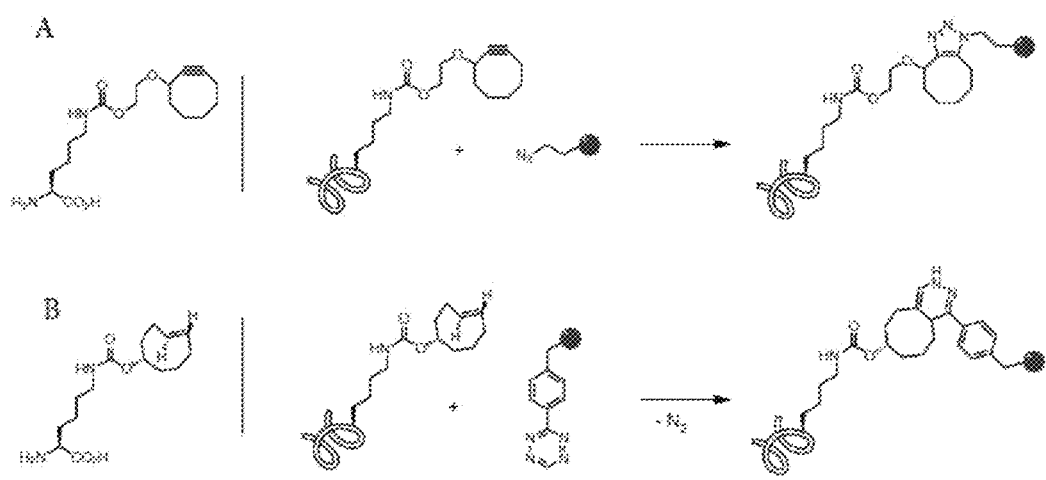
FIGS. 17A-17B depict NSAAs suitable for use according to certain exemplary embodiments of the invention (Kim et al. (2013) *Curr. Opin. Chem. Biol.* 17:412).

Most of the best candidates showed normal growth phenotype in the presence of bipA (FIG. 13). Best candidates had a range of escape frequencies (FIG. 14).

EXAMPLE IV

Additional Strategies

Escape mechanisms are determined using, e.g., NNN oligos and next-generation sequencing methods. Best candidates are combined by conjugation, e.g., mutS+, bipA synthetase on genome, and/or multiplicative effect from orthogonal escape routes.

Saturation mutagenesis is performed for all recoded sites and tRNAs to ensure that there are no pathways to escape.

X-ray structures are solved for essential proteins with NSAAs in redesigned cores Environmental studies of safe genetically modified organisms are performed using a variety of substrates including, but not limited to, soil, water, waste, compost, and the like.

Conjugation studies to assess escape of safe genetically modified organisms due to horizontal gene transfer are performed.

Additional codons are reassigned to increase the genetic isolation of genetically modified organisms.

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. A genetically modified *Escherichia coli* (*E. coli*) cell comprising:
   an essential polypeptide encoded by an essential nucleic acid sequence, wherein the essential polypeptide comprises a recoded adenylate kinase (adk) comprising I4A, L6V, V103A, L178bipA, Y182V, and T191I substitutions; a recoded alanyl-tRNA synthetase (alaS) comprising M1bipA, F90A, F293A, L338bipA, M342A, and L349P substitutions; a recoded methionyl-tRNA synthetase (metG) comprising M485A, F502G, and L503bipA substitutions; a recoded phosphoglycerate kinase (pgk) comprising V185A, I187A, I211G, and L297bipA substitutions; or a recoded tyrosol-tRNA synthetase (tyrS) comprising F706A, W778F, T787V, F823G, L907bipA, and V919A substitutions, wherein bipA is L-4,4'-bisphenylalanine.

2. The cell of claim 1, comprising two or more essential polypeptides encoded by two or more essential nucleic acid sequences.

3. The cell of claim 1 wherein the essential polypeptide comprises the recoded adk comprising I4A, L6V, V103A, L178bipA, Y182V, and T191I substitutions.

4. The cell of claim 1 wherein the essential polypeptide comprises the recoded alaS comprising M1bipA, F90A, F293A, L338bipA, M342A, and L349P substitutions.

5. The cell of claim 1 wherein the essential polypeptide comprises the recoded metG comprising M485A, F502G, and L503bipA substitutions.

6. The cell of claim 1 wherein the essential polypeptide comprises the recoded pgk comprising V185A, I187A, I211G, and L297bipA substitutions.

7. The cell of claim 1 wherein the essential polypeptide comprises the recoded tyrS comprising F706A, W778F, T787V, F823G, L907bipA, and V919A substitutions.

* * * * *